United States Patent
Govrin et al.

(10) Patent No.: US 12,232,692 B2
(45) Date of Patent: *Feb. 25, 2025

(54) INTEGRATED ENDOSCOPE IRRIGATION

(71) Applicant: SCOUTCAM LTD., Omer (IL)

(72) Inventors: Amir Govrin, Ramat Gan (IL); Yekaterina Dlugach, Mabuim (IL); Tsafrir Kolatt, Zichron Ya'akov (IL)

(73) Assignee: SCOUTCAM LTD., Omer (IL)

(*) Notice: Subject to any disclaimer, the term of this patent is extended or adjusted under 35 U.S.C. 154(b) by 443 days.

This patent is subject to a terminal disclaimer.

(21) Appl. No.: 17/585,797

(22) Filed: Jan. 27, 2022

(65) Prior Publication Data
US 2022/0142456 A1   May 12, 2022

Related U.S. Application Data

(63) Continuation of application No. 16/661,202, filed on Oct. 23, 2019, now Pat. No. 11,266,300, which is a continuation of application No. 15/592,252, filed on May 11, 2017, now Pat. No. 10,492,662, which is a continuation-in-part of application No. 14/385,185, filed as application No. PCT/IL2013/050170 on Feb. 28, 2013, now abandoned.

(60) Provisional application No. 61/616,097, filed on Mar. 27, 2012.

(51) Int. Cl.
*A61B 1/00* (2006.01)
*A61B 1/015* (2006.01)
*A61B 1/005* (2006.01)

(52) U.S. Cl.
CPC .......... *A61B 1/00091* (2013.01); *A61B 1/015* (2013.01); *A61B 1/0052* (2013.01)

(58) Field of Classification Search
CPC ... A61B 1/00091; A61B 1/015; A61B 1/0052; A61B 1/00089; A61B 1/00101; A61B 1/00137
See application file for complete search history.

(56) References Cited

U.S. PATENT DOCUMENTS

| | | | |
|---|---|---|---|
| 3,610,231 | A | 10/1971 | Takahashi et al. |
| 4,607,622 | A | 8/1986 | Fritch et al. |
| 4,779,612 | A | 10/1988 | Kishi |

(Continued)

FOREIGN PATENT DOCUMENTS

| | | | |
|---|---|---|---|
| CN | 2885155 | Y | 4/2007 |
| CN | 103976763 | A | 8/2014 |

(Continued)

OTHER PUBLICATIONS

Sugar, A. (2016) 2-6 Hydrodissection and Hydrodelineation, Syrian Board of Ophthalmology in YouTube web page, minutes: 0:43-1:46, https://www.youtube.com/watch?v=YpiCkOAq9dQ.

(Continued)

*Primary Examiner* — Timothy J Neal
(74) *Attorney, Agent, or Firm* — The Roy Gross Law Firm, LLC; Roy Gross

(57) ABSTRACT

A distal tip of an endoscopic device and a cylindrical cap is disclosed. The distal tip comprises a pattern of alternating grooves and lands on its outer surface. The cylindrical cap is configured to fit tightly over the lands, thereby changing the grooves into closed channels through which liquid or gas can flow.

20 Claims, 7 Drawing Sheets

(56) References Cited

U.S. PATENT DOCUMENTS

| | | | |
|---|---|---|---|
| 4,867,138 A | 9/1989 | Kubota et al. | |
| 4,919,112 A * | 4/1990 | Siegmund | A61B 1/0052 |
| | | | 600/146 |
| 4,950,278 A | 8/1990 | Sachse et al. | |
| 5,323,766 A | 6/1994 | Uram | |
| 5,575,756 A * | 11/1996 | Karasawa | A61B 1/0014 |
| | | | 600/156 |
| 5,685,823 A | 11/1997 | Ito et al. | |
| 5,797,849 A | 8/1998 | Vesely et al. | |
| 6,398,721 B1 | 6/2002 | Nakamura et al. | |
| 6,447,444 B1 | 9/2002 | Avni et al. | |
| 6,447,445 B1 | 9/2002 | Hirano | |
| 7,954,607 B2 | 6/2011 | Kallioniemi et al. | |
| 8,226,548 B2 | 7/2012 | Kucklick | |
| 8,622,896 B1 | 1/2014 | Termanini | |
| 9,750,638 B2 | 9/2017 | Bourne et al. | |
| 10,492,662 B2 | 12/2019 | Govrin et al. | |
| 2003/0088260 A1 | 5/2003 | Smedley et al. | |
| 2006/0020165 A1 | 1/2006 | Adams | |
| 2007/0015961 A1 | 1/2007 | Yamamoto et al. | |
| 2007/0129605 A1 | 6/2007 | Schaaf | |
| 2008/0091074 A1 | 4/2008 | Kumar et al. | |
| 2008/0167527 A1 | 7/2008 | Slenker et al. | |
| 2008/0214891 A1 | 9/2008 | Slenker et al. | |
| 2008/0214895 A1 * | 9/2008 | Campos | A61B 1/307 |
| | | | 600/129 |
| 2009/0253964 A1 | 10/2009 | Miyamoto | |
| 2010/0305503 A1 | 12/2010 | Fang et al. | |
| 2010/0331658 A1 | 12/2010 | Kim et al. | |
| 2011/0112405 A1 | 5/2011 | Barthe et al. | |
| 2011/0152618 A1 | 6/2011 | Surti | |
| 2012/0197084 A1 | 8/2012 | Drach et al. | |
| 2012/0265010 A1 | 10/2012 | Uram | |
| 2012/0289858 A1 | 11/2012 | Ouyang et al. | |
| 2013/0172674 A1 * | 7/2013 | Kennedy | A61B 1/00195 |
| | | | 600/109 |
| 2013/0205936 A1 | 8/2013 | Schmieding et al. | |
| 2014/0309649 A1 | 10/2014 | Alvarez et al. | |
| 2015/0025539 A1 | 1/2015 | Alvarez et al. | |
| 2015/0045820 A1 | 2/2015 | Kahook | |
| 2015/0141755 A1 | 5/2015 | Tesar | |
| 2015/0297407 A1 | 10/2015 | Saimovici | |
| 2016/0143778 A1 | 5/2016 | Aljuri et al. | |
| 2016/0166134 A1 | 6/2016 | Sonnenschein et al. | |
| 2016/0287332 A1 | 10/2016 | Griffits | |
| 2018/0055596 A1 | 3/2018 | Johnson | |
| 2018/0078410 A1 | 3/2018 | Gavanescu | |
| 2018/0110404 A1 | 4/2018 | Devaiah et al. | |
| 2018/0125707 A1 | 5/2018 | Khaderi et al. | |
| 2019/0298321 A1 | 10/2019 | Intintoli et al. | |

FOREIGN PATENT DOCUMENTS

| | | |
|---|---|---|
| CN | 104224441 A | 12/2014 |
| CN | 204207828 U | 3/2015 |
| EP | 1794486 A | 6/2007 |
| GB | 2268883 A | 1/1994 |
| JP | H07100096 A | 4/1995 |
| JP | H09238896 A | 9/1997 |
| JP | 2009056255 A | 3/2009 |
| JP | 2009274874 A | 11/2009 |
| RU | 2177286 C2 | 2/2001 |
| WO | 200271991 A2 | 9/2002 |
| WO | 2004026125 A1 | 4/2004 |
| WO | 2017100651 A1 | 6/2017 |

OTHER PUBLICATIONS

AISCO opthalmic surgical Instruments catalog 2013, pp. 152-154.
GEUDER Ophthalmic Surgical Products—Instruments Main Catalog 2018, pp. 192-194.
Hydrodissection, Boston University School of Medicine, Department of Ophthalmology, webpage, Mar. 8, 2019.

* cited by examiner

INTEGRATED ENDOSCOPE IRRIGATION

CROSS REFERENCE TO RELATED APPLICATIONS

This application is a continuation of U.S. patent application Ser. No. 16/661,202 filed on Oct. 23, 2019, which is a continuation of U.S. patent application Ser. No. 15/592,252, filed on May 11, 2017 and Issued as U.S. patent Ser. No. 10/492,662 on Dec. 3, 2019, which is a continuation-in-part of U.S. patent application Ser. No. 14/385,185, filed on Sep. 15, 2014, which is a National Phase of PCT/IL2013/050170 having International filing date of Feb. 28, 2013, which claims the benefit of priority of U.S. Provisional Patent Application No. 61/616,097, filed on Mar. 27, 2012, the contents of which are all incorporated herein by reference in their entirety.

FIELD OF THE INVENTION

The invention is from the field of medical devices. More specifically, the invention is from the field of small diameter endoscopic devices.

BACKGROUND OF THE INVENTION

In various medical applications there are many advantages for using small diameter endoscopes and laparoscopes (collectively called endoscopes or endoscopic devices herein) having, for example, a maximum outer diameter of 3.2 mm. Most importantly small diameter endoscopes can be introduced to desired locations within the body through small diameter natural orifices and lumens. Also in cases where introduction of the endoscope may be irritating, a small diameter endoscope may mitigate such phenomena. An example of a procedure in which small diameter endoscopes can be useful is transnasal endoscopy that in some cases may replace trans-oral endoscopy. Moreover, small diameter endoscopes may be introduced into body cavities by single incision laparoscopy, wherein the incision itself is of minimal dimensions.

By its nature, endoscopy entails incorporating many components adapted to perform various functions within a single elongated instrument. This fact sometimes conflicts with the desire for minimum diameter and size in general. Among these components are: imaging devices, e.g. video cameras; illumination devices, e.g. optical fibers or LEDS; articulation means; tissue collection devices or other surgical tools; irrigation, insufflation, and more.

One of the ways to accommodate as many components and functions as possible is to decrease the size of each individual component, e.g., using a smaller size camera or a smaller size fiber bundle. However, this is not always possible. There are limits to how much size reduction can be achieved since each size reduction has its cost in terms of performance and assembly complexity.

It is therefore a purpose of the present invention to provide a method of reducing the diameter of endoscope devices.

It is another purpose of the present invention to provide a method of providing an endoscopic device with more components without increasing the cross section of the insertion tube.

Further purposes and advantages of this invention will appear as the description proceeds.

SUMMARY OF THE INVENTION

In a first aspect the invention is an endoscopic device that comprises a handle section, an insertion tube connected to the handle section, a distal tip at the distal end of the insertion section, and a plurality of tubes, wires, and cables that pass through the interior of the insertion tube, and empty spaces between the plurality of tubes, wires, and cables. The empty spaces are utilized as a channel that enables liquid or gas to flow from the handle section to the distal tip. The endoscopic device is characterized in that the distal tip comprises a block having a pattern of alternating grooves and lands on its outer surface and a cap comprising a hole at the center of the distal surface of the cylindrical cap. The hole is surrounded by an annular curved portion. The cap fits tightly over the lands thereby forming channels between the lands through which liquid or gas flowing through the empty spaces can continue on its way to at least one nozzle that is formed by a gap between the front face of the block and the bottom surface of the annular curved portion of the cap.

Embodiments of the endoscopic device comprise at least one of:

(a) an articulation section located at the distal end of the insertion tube proximally to the distal tip, the articulation section is activated by cables or wires that pass through tubes that extend the length of the interior of the insertion tube from the handle section to the articulation section;

(b) an imaging device located in the distal tip, the imaging device activated by power delivered to it and transmitting images gathered by it via one or more cables, wires, or optical fibers that pass through one or more tubes that extend the length of the interior of the insertion tube from the handle section to the distal tip;

(c) illumination devices located in the distal tip, the illumination devices are activated by wires or optical fibers that pass through one or more tubes that extend the length of the interior of the insertion tube from the handle section to the distal tip;

(d) one or more working channels that pass through the interior of the insertion tube from the handle section to the distal tip;

(e) one or more other components each of which is located at a location on the insertion tube or on the distal tip and is associated with a tube, wires, or cable that passes through the interior of the insertion tube from the handle section to the location.

Embodiments of the endoscopic device comprise the handle section comprises components of an articulation mechanism including articulation cylinders that are sealed by gaskets, which are adapted to enable movement of the cables or wires that pass through the insertion tube to steer the articulation section without leakage of liquid or gas between the handle section and the insertion tube.

In embodiments of the endoscopic device the imaging device is a video camera.

In embodiments of the endoscopic device the components located at a location on the insertion tube or on the distal tip are selected from: lasers and radio frequency generators.

In a second aspect the invention is a method of reducing the diameter of an endoscope device that comprises a handle section, an insertion tube connected to the handle section, a distal tip comprising a block and a cap attached to the insertion tube, and a plurality of tubes including at least one tube that serves as a liquid or gas channel, wires, and cables that pass through the interior of the insertion tube. The method comprises:

a) creating a pattern of alternating grooves and lands on the outer surface of the block of the distal tip;

b) removing the at least one tube that serves as a liquid or gas channel and allowing liquid or gas to flow from the handle section to the distal tip through empty spaces between the plurality of tubes, wires, and cables; and c) fitting the cap over the block, wherein the cap comprises a hole at the center of its distal surface surrounded by an annular curved portion and the cap fits tightly over the lands thereby forming channels between the lands through which the liquid or gas flowing through the empty spaces can continue to flow to at least one nozzle formed by a gap between the front face of the block and the bottom surface of the annular curved portion of the cap.

In the endoscopic device of the second aspect, the total cross sectional areas of the empty spaces is as large as or larger than the cross sectional area of the at least one tube that has been removed, thereby allowing at least the same amount of fluid can be delivered to the distal tip through the insertion tube after reducing its diameter as was delivered through the tube that was removed.

In embodiments of the method the liquid or gas that flows through the empty spaces between the plurality of tubes, wires, and cables that pass through the interior of the insertion tube from the handle section of the endoscope to the at least one nozzle is used for at least one of the following purposes: irrigation, insufflation, suction, cooling, heating, staining tissue, and therapy.

In a third aspect the invention is a distal tip comprising a block having a pattern of alternating grooves and lands on its outer surface and a cap. Channels through which liquid or gas can flow are formed on the outer surface of the distal tip by a fitting the cap tightly over the lands on the outer surface of the block.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Endoscopic devices are comprised of a handle section, an elongated insertion tube, and a distal tip at the end of the insertion section. An articulation section is often included at the distal end of the insertion section just before the distal tip to allow the distal tip to be deflected in order to change the angle of view of the imaging device and to aid in steering the insertion tube through bodily lumens to the location where the observations or procedure are to be carried out. To prevent bodily fluids, tissue, or debris from entering the insertion tube, it and the articulation section are encased in a sheath of polymeric material.

The present invention is directed to endoscopic devices that typically comprise at least an imaging device, e.g. a video camera and accompanying illumination means in the distal tip and optionally may include an articulation section that is activated by cables or wires that pass through the interior of the insertion tube from an articulation steering mechanism located in the handle section. Endoscopic devices frequently also comprise one or more working channels, through which surgical tools, e.g. forceps, snares, and therapy devices, e.g. lasers or RF generators, can be introduced from the handle section to the space beyond the distal tip in order to collect samples or carry out various procedures. In addition there are frequently channels for other purposes, e.g. irrigation water or air to clean the camera lens, gas for insufflation, dye for staining tissue, liquid for cooling (or heating), and gas or liquid for therapy, e.g. delivery of drugs or medicine.

In present day endoscopic devices each of the working channels and the channels for irrigation and insufflation are small tubes that run through the insertion tube from handle to distal tip. As an alternative to having separate tubes for each component or function, endoscopes may comprise a multi-lumen tube which contains separate lumens for each component. Also the optical fibers or electric wires for the illumination means and the power and signal wires to and from the camera pass through similar tubes. All of these individual tubes and the articulation cables or wires are tightly packed into the interior of the insertion tube.

Figure 5A:
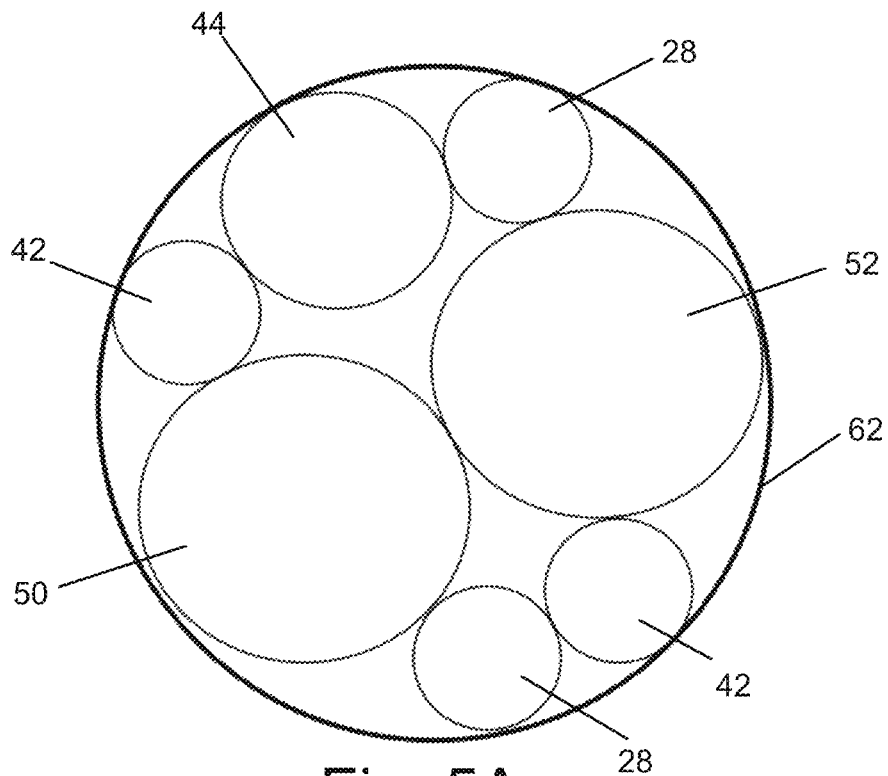
FIG. 5A schematically shows a transverse cross-section of a typical prior art insertion tube comprising a water tube at a location between the handle and the articulation section.
Figure 5B:
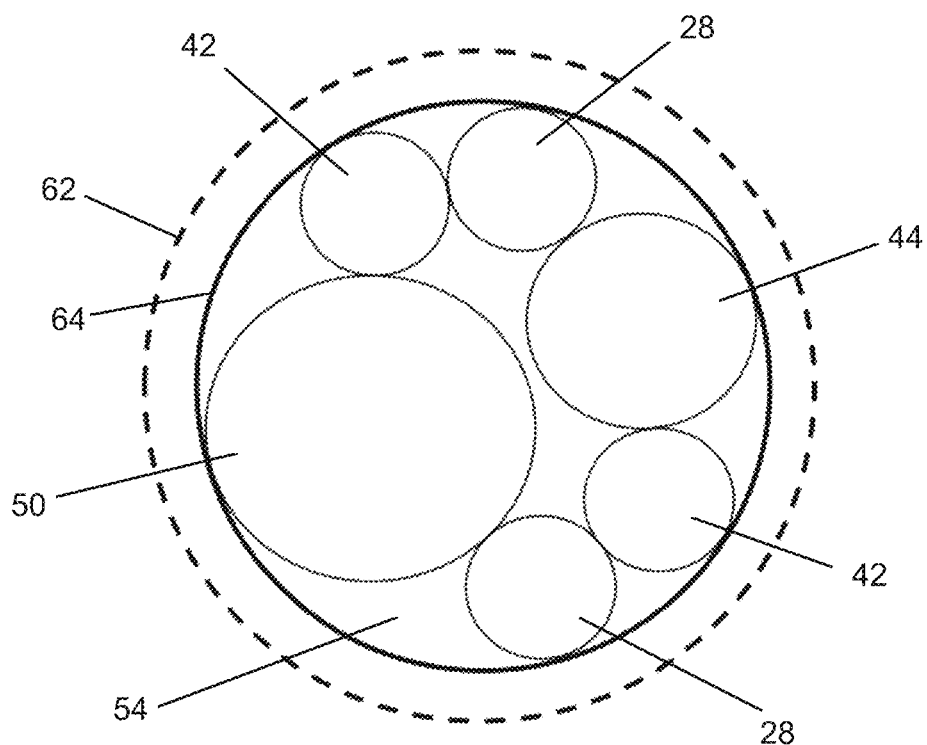
FIG. 5B schematically shows a transverse cross-section of a typical insertion tube not comprising a water tube at a location between the handle and the articulation section.

FIG. 5A and FIG. 5B illustrate how the diameter of the insertion tube of an endoscopic device can be reduced by removing the water channel according to the present invention.

FIG. 5A schematically shows a transverse cross-section of a typical insertion tube at a location between the handle and the articulation section. In the figure can be seen how two illumination fibers 28, camera cable 44, two articulation cables 42, a tube for a working channel 50, and a tube for a water channel 52 are fit into the interior of insertion section 14. The circumference of the insertion tube in FIG. 5A is denoted by reference symbol 62.

FIG. 5B is a transverse cross sectional view of an insertion tube that, with the exception that there is no tube for a water channel, contains the same tubes, illumination fibers, and cables having the same diameters as those in FIG. 5A. Water travels through the insertion tube in FIG. 5B through the empty spaces 54 (only one is marked in FIG. 5B) between the other components passing through the insertion section. The circumference of the insertion tube in FIG. 5B is denoted by reference symbol 64.

As can be seen from FIGS. 5A and 5B, packing a plurality of tubes having a circular cross-section into a larger cylindrical tube inevitable means that there will be empty spaces between the tubes that are not utilized. The current invention makes use of these spaces to allow fluid to flow from the handle of the endoscope to the distal tip. In this way it is not necessary to have a separate irrigation/insufflation/cooling/dye/therapy channel and as a result the overall diameter of the insertion tube can be reduced as demonstrated by the comparison of circumference 64 in FIG. 5B with circumference 62 (shown with a dashed line in FIG. 5B for comparison) of the insertion tube of FIG. 5A. It should also be noted that the cross sectional area of each of the spaces 54 in FIG. 5B is less than the cross sectional area of the tube 52 (from FIG. 5A) that has been removed; however the total cross-section of all spaces 54 is equal to or larger than that of tube 54. This means that at least the same amount of fluid can be delivered to the nozzle at the distal tip through the insertion tube in FIG. 5B as through that of FIG. 5A despite the smaller overall diameter of the insertion tube.

Alternatively to reducing the diameter of the insertion tube, the invention allows the space formally occupied by the tube for a water channel to be utilized to pass additional components, e.g. an additional working channel, through the insertion tube.

FIG. 1 to FIG. 4 and FIG. 6 to FIG. 9 illustrate embodiments of an endoscope built according to the present invention.

Figure 1:
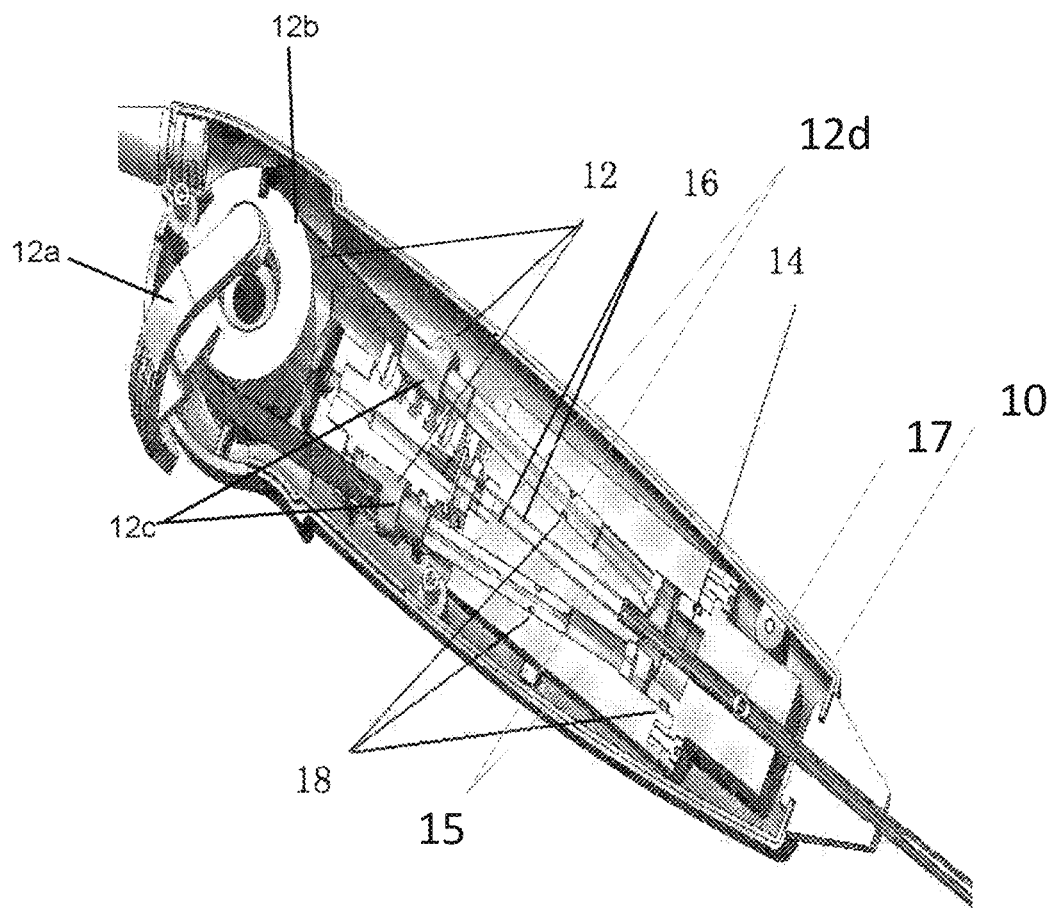
FIG. 1 schematically shows some of the interior components of the handle section of an endoscopic device.

FIG. 1 schematically shows a base part 10 of the handle section of an embodiment of an endoscopic device with the cover partially removed to reveal some of the interior components. Shown in FIG. 1 are the articulation handle 12 *a*, articulation drum 12 *b*, articulation cylinders 12*c* and articulation cables or wires 12*d* of articulation mechanism 12; insertion tube 14; illumination fibers and power and signal wires 16; and gaskets 18.

When the cover of the handle section is in place it presses against the gaskets 18 forming an air and water tight compartment 15 in the handle. In particular the two small O-rings seal the articulation cylinders and enable movement of the steering (articulation) cables or wires 12*d* without leakage of fluid. An inlet port 17 allows water for irrigation or gas for insufflation to be introduced into this compartment. As will be described herein below, the water or gas flows out of the compartment in the handle into and through the insertion tube and exits the endoscope through a nozzle (or a set of nozzles) located on the distal tip.

Conventional endoscopic distal tips are made from a monolithic cylindrical block of metal or plastic comprising bores that pass through the block from its proximal end to its distal face to allow components of the insertion tube such as illumination fibers, camera cable, and working channels to pass from one side of the distal tip to the other via these bores. Additionally there can be cavities created on the front surface of the block to hold components such as a camera head or LEDs. For these distal tips the external surfaces of the block are smooth and shaped to minimize trauma as the endoscope is advanced to the site of the procedure.

In contrast to conventional distal tips, the distal tip of the present invention is comprised of two components: a) a block 22 comprising a pattern of alternating grooves 32 and lands 34 that are created on its outer surface; and b) a cap 24, which fits tightly over the lands 34 to provide the distal tip with a smooth outer surface. The tops of lands 34 are pressed against the inside wall of cap 24 forming hermetic seals that effectively convert grooves 32 into closed channels through which water or gas flowing through the insertion tube can continue on its way to a nozzle on the distal end of the endoscope.

Figure 2:
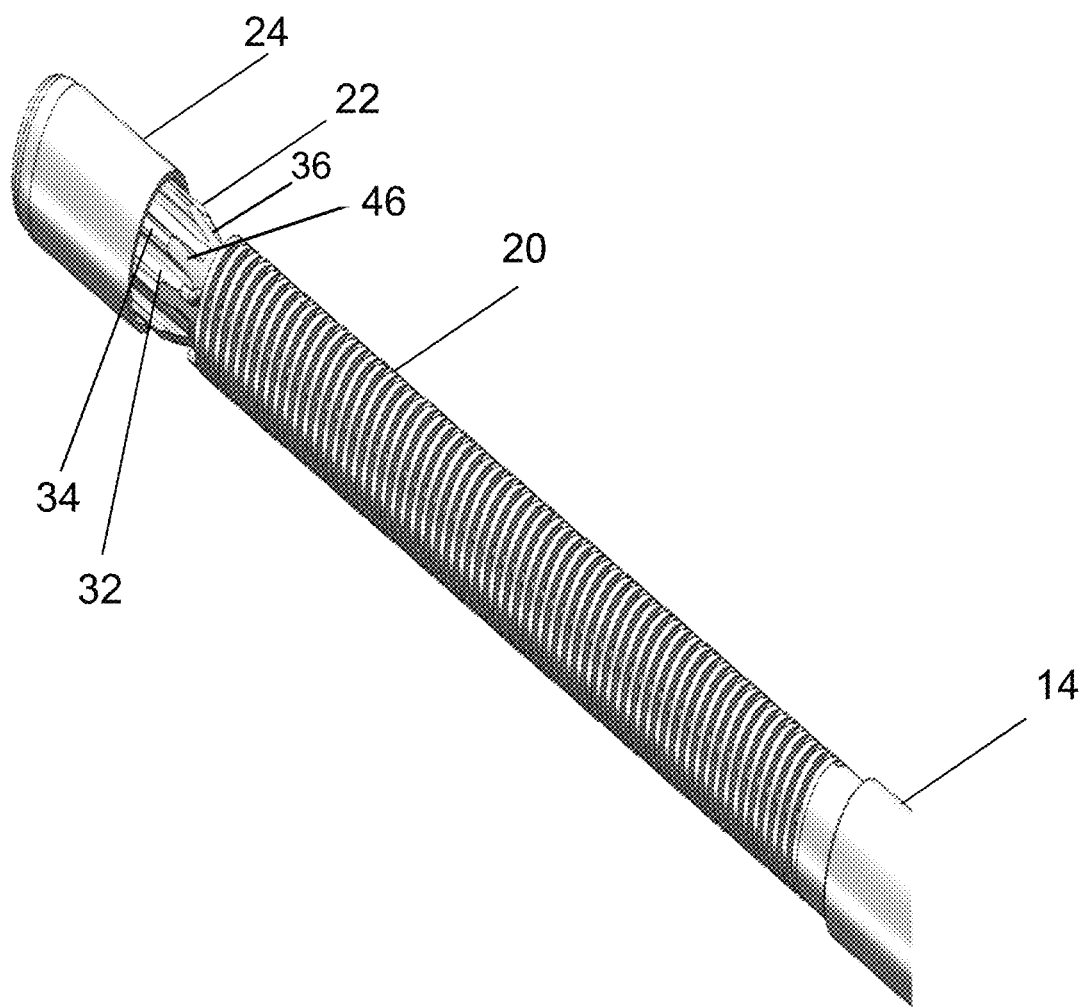
FIG. 2 schematically shows an articulation section and a distal tip at the distal end of a first embodiment of an insertion tube that can be connected to the handle section shown in FIG. 1.

FIG. 2 schematically shows the distal end of an insertion tube 14 that can be connected at its proximal end to the handle section shown in FIG. 1. The sheath that covers the insertion tube has been removed to reveal articulation section 20 and the distal tip comprised of block 22 and cap 24.

Also seen in FIG. 2 are tabs 46 and the tapered proximal end 36 of block 22. Tabs 46 symbolically represent one way of connecting block 22 of the distal tip to insertion tube 14. The tabs can be attached by any method known in the art, e.g. welding or gluing, to the distal end of articulation section 20 and to the tops of the proximal ends of lands 34 on the outer surface of block 22. In other embodiments the block acts as or is attached directly to the distal link of the articulation section. The function of tapered proximal end 36 will be described herein below.

Figure 3:
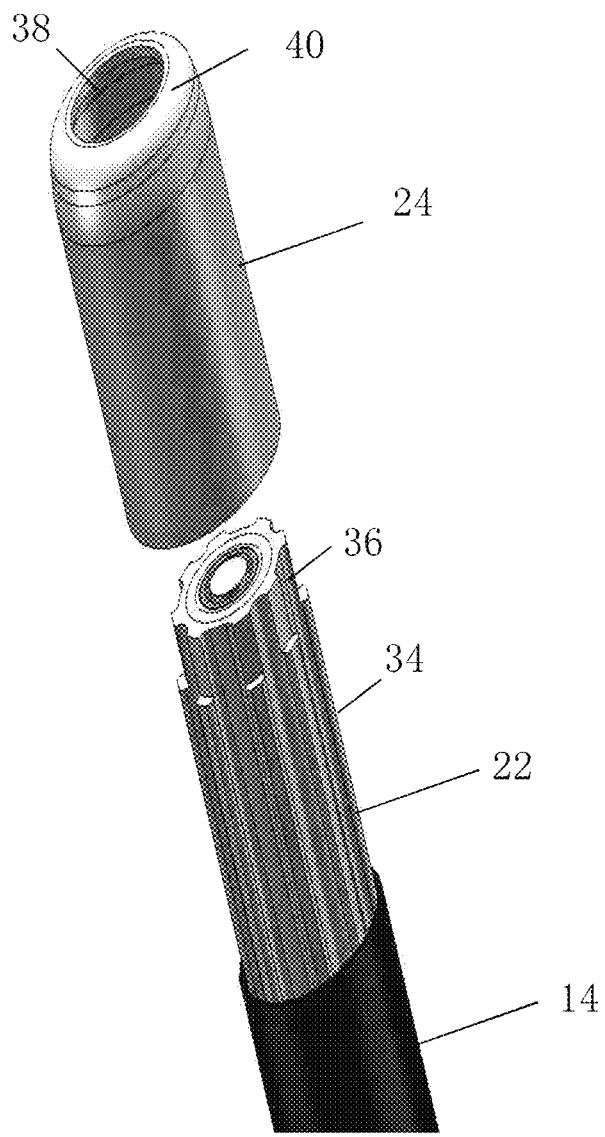
FIG. 3 schematically shows an enlarged view of the distal tip shown in FIG. 2.
Figure 4:
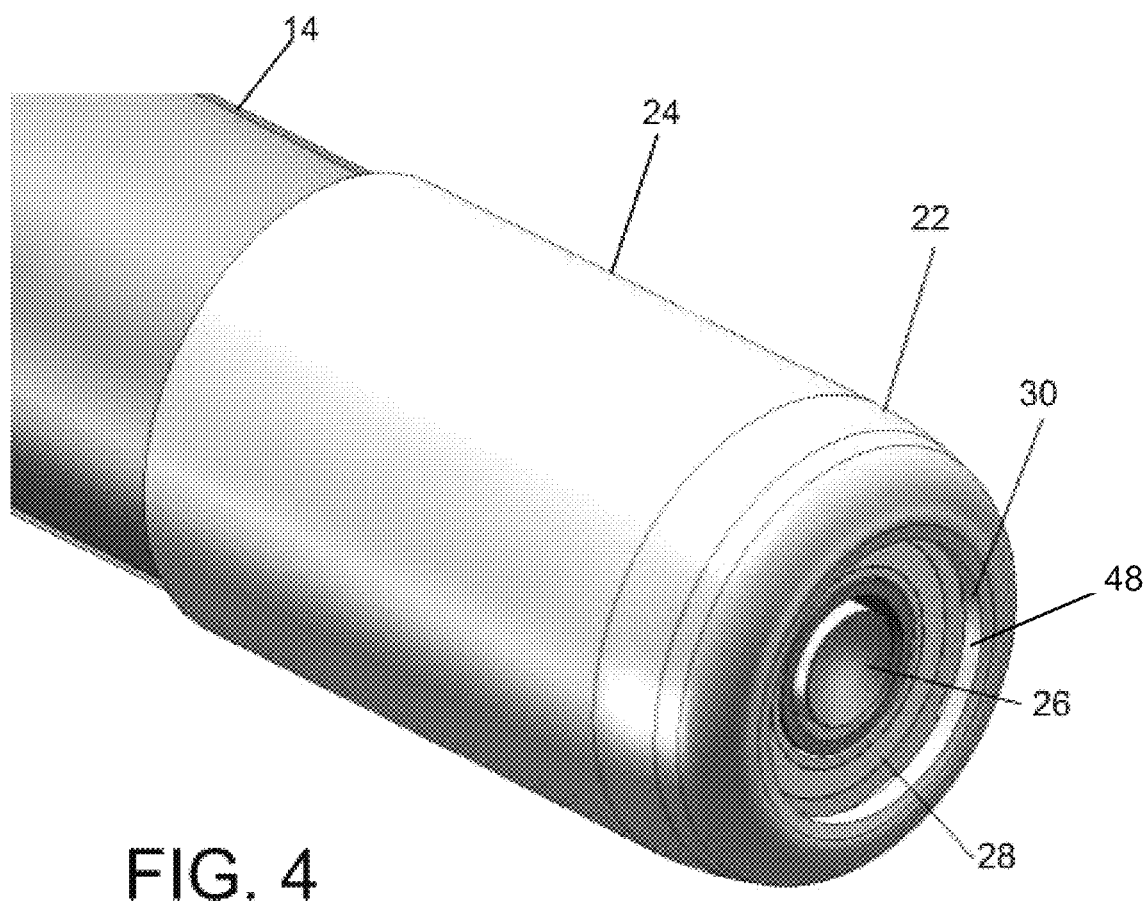
FIG. 4 schematically shows the face of the distal tip shown in FIG. 2.
Figure 6:
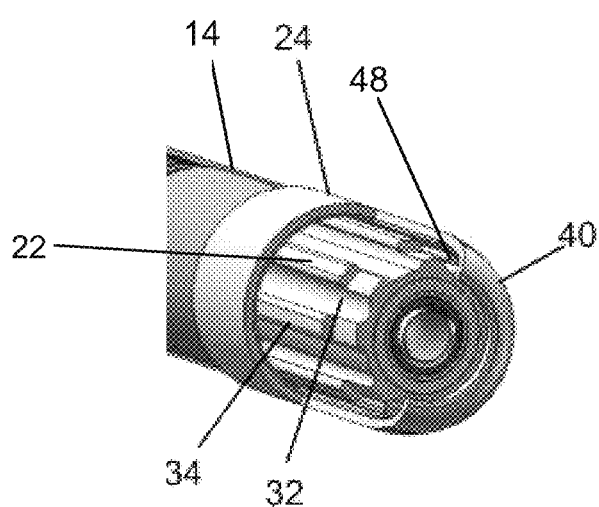
FIG. 6 schematically shows the distal tip of the endoscopic device shown in FIG. 4 with part of the cap removed.

FIG. 3 schematically shows an enlarged view of the distal tip shown in FIG. 2 with the cap 24 completely removed from the block 22 and FIG. 4 schematically shows cap 24 completely covering block 22. FIG. 6 schematically shows the distal tip of the endoscopic device shown in FIG. 4 with part of the cap 24 cut away. In the embodiment shown in FIGS. 2, 3, 4, and 6 a cable for camera 26 and illumination fibers leading to light ring 58 pass through insertion tube 14.

Figure 7:
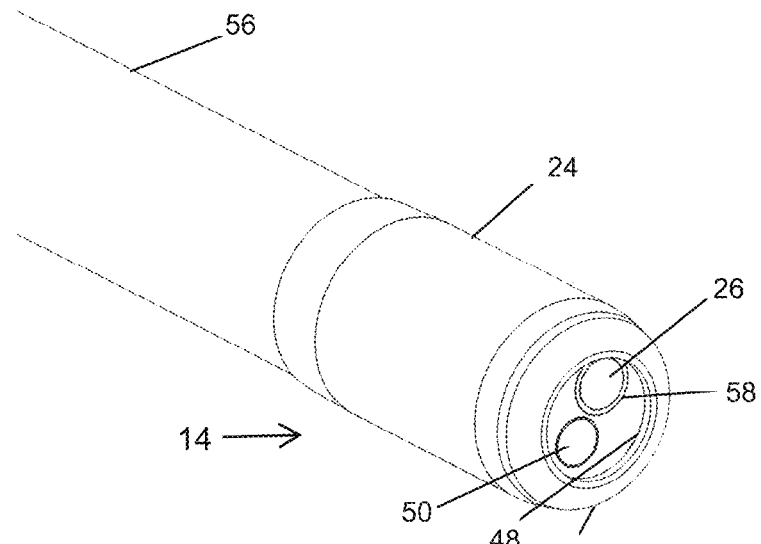
FIG. 7 schematically shows the distal end of a second embodiment of an insertion tube that can be connected to the handle section shown in FIG. 1.
Figure 8:
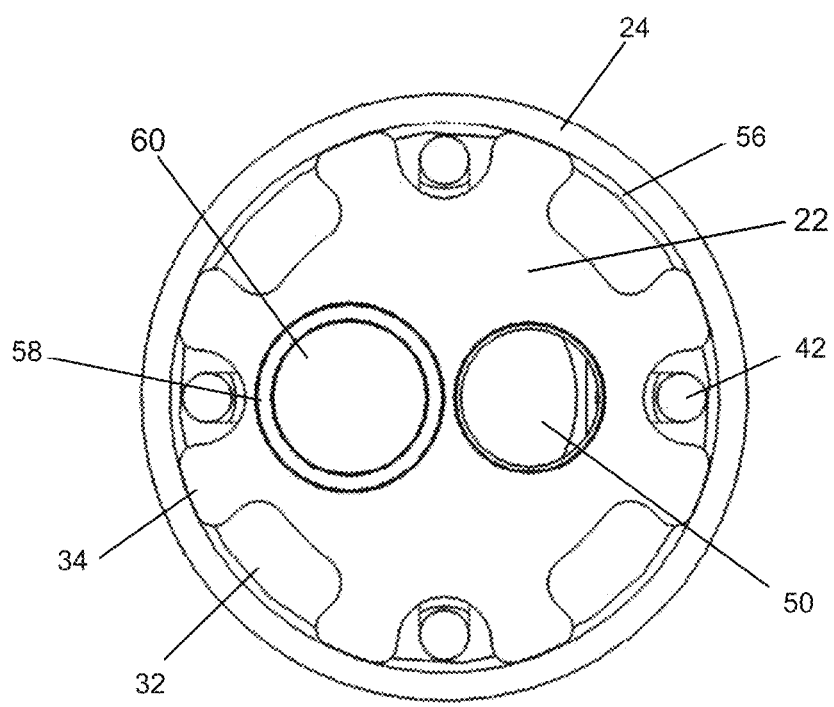
FIG. 8 schematically shows a transverse cross sectional view through the distal tip of the endoscopic device of FIG. 7.
Figure 9:
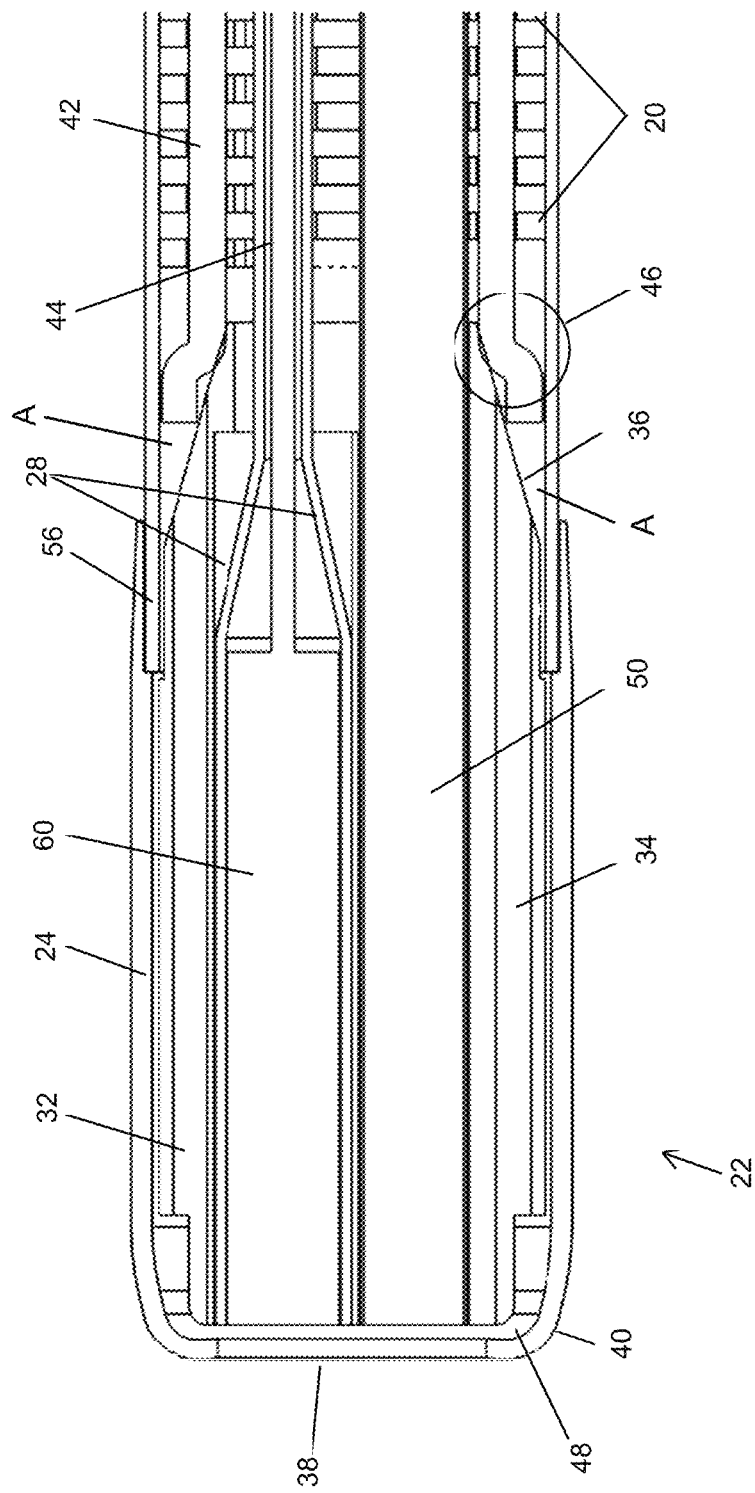
FIG. 9 schematically shows a longitudinal cross sectional view of the distal end of the endoscopic device of FIG. 7.

FIG. 7 schematically shows the distal end of a second embodiment of an insertion tube that can be connected to the handle section shown in FIG. 1. FIG. 8 and FIG. 9 respectively schematically show a transverse cross sectional view and a longitudinal cross sectional view through the distal tip of the endoscopic device of FIG. 7. In the embodiment shown in FIGS. 7, 8, and 9, in addition to the components shown in the previous embodiment a working channel 50 passes through insertion tube 14.

The method in which a nozzle (or nozzles) are created at the distal tip of the endoscopic device and the manner in which the fluid travels from the compartment in the handle to the nozzle is the same for both embodiments.

As shown in FIG. 3, a circular portion at the center of the distal surface of cylindrical cap 24 is removed leaving a hole 38 surrounded by an annular curved portion 40. As can also be seen in the same figure, a part 35 of the distal end of each land 34 is removed, With the insertion section 14, including the articulation section, completely covered with the sheath 56 and the cap 24 in place over the block 22 as shown in FIGS. 4, 6, 7, and 9 the inside of the endoscope is hermetically isolated from the outside with the exception of a small gap 48 between the front face of the block 22 and the bottom of curved surface 40 around the circumference of hole 38 in cap 24. The shape of curved surface 40 causes the gap 48 to function as a circular nozzle 30.

Water or gas introduced into the compartment in the handle enters the insertion tube 14 and flows through the empty spaces 54 between the tubes and cables that pass through insertion tube 14 and articulation section 20. On reaching block 22, the fluid travelling down the insertion tube the tapered proximal end 36 and is forced to the sides and through the grooves. The water or gas flows through grooves 32 and out of the distal end through circular nozzle 30. The components of the distal tip are configured such that water or gas exiting through circular nozzle 30 is sprayed over the illumination fibers 28 and objective lens of camera 26 keeping them clean. It is noted that tapering the proximal ends of block 22 is one of several ways that could be employed to allow the fluid to flow from the handle at the proximal end to a nozzle or nozzles at the distal end of the endoscopic device.

FIG. 6 shows the distal tip of the endoscopic device shown in FIG. 4 with part of the cap 24 removed to reveal the lands 34 and grooves 32 on the outside surface of block 22 and the gap 48 between the front face of block 22 and the bottom of curved surface 40 of cap 24 that functions as circular nozzle 30.

FIG. 7 schematically shows the distal end of an embodiment of endoscopic device. Seen in this figure is sheath 56 covering the insertion tube and distal tip 14. A camera 26, light ring 58, and working channel 50 are seen on the front face of the distal tip. Gap 48 is seen between the bottom of the curved portion 40 of the cap 24 that covers the block 22 of the distal tip.

FIG. 8 schematically shows a transverse cross sectional view through the distal tip of the endoscopic device of FIG. 7. Seen in the figure are working channel 50, a cavity 26 for a camera head, and light ring 58. Also seen are the lands 34 and grooves 32 on the surface of the block 22, the cap 24 that fits tightly over the lands and overlaps the sheath 56, and articulation cables 42.

FIG. 9 schematically shows a longitudinal cross sectional view of the endoscopic device of FIG. 7. Seen in this figure are articulation section 20 and articulation cables 42. The distal end of each articulation cable 42 is bent to form a sort of tab 46 that is fixedly attached to the proximal end of block 22, for example by soldering or welding, thereby attaching the distal tip 22 to the articulation section 20. The proximal part 36 of block 22 is cut at an angle to allow water flowing through the insertion tube between the tubes and cables enclosed by sheath 56 to enter the grooves 32 between lands 34 and to flow through the grooves 32 to the curved annular end 40 of cap 24 that covers the grooves 32 and lands 34. When water reaches curved annular end 40 it flows through gap 48 and is sprayed over the front face of block 22 exiting through hole 38. Also seen are channels for the camera cable 44 and illumination fibers 28, working channel 50, and a cavity 60 into which a camera head can be inserted.

The embodiments described herein are configured to comprise a circular nozzle, i.e. a nozzle that creates a spray emitted in all (360 degrees) directions. In other embodiments the grooves 32, lands 34 and hole 38 in the cap 24 can be configured to direct the liquid or gas to form one or more nozzles that will emit a spray having any desired angular spread.

It is noted that only very basic embodiments of an endoscopic device have been described herein in order to illustrate the principle of the invention. In addition to a working channel, camera and illumination means, the endoscope may comprise additional working channels, and other components located on the distal tip, e.g. ultrasound transducers. All of these require their own tube, cable, or wire that must be integrated into the interior of the insertion tube. In these embodiments, eliminating the need for a separate irrigation and/or insufflation channel by utilizing the spaces between the other tubes for the passage of water or gas as taught by the present invention will play an important role in reducing the overall diameter of the insertion tube.

Although embodiments of the invention have been described by way of illustration, it will be understood that the invention may be carried out with many variations, modifications, and adaptations, without exceeding the scope of the claims.

The invention claimed is:

1. A handle of an endoscopic device connected to an insertion tube comprising an articulation section located at a distal end of the insertion tube, the handle comprising:
    an articulation mechanism including articulation cables or wires passing through the insertion tube to steer the articulation section, wherein at least a portion of the articulation cables or wires are provided in one or more fluid sealed compartments, the one or more fluid sealed compartments being sealed relative to the handle to prevent leakage of liquid or gas from the compartments into the handle while allowing the passage of liquid from the one or more fluid sealed compartments through the insertion tube.

2. The handle of claim 1, wherein the one or more fluid sealed compartments are sealed by one more gaskets.

3. The handle of claim 2, wherein the handle comprises a base part and a cover and wherein the cover of the handle is configured to press against the gaskets, thereby forming said one or more fluid sealed compartments in the handle.

4. The handle of claim 2, wherein the gaskets comprise at least one O-ring configured to seal the one or more fluid sealed compartments and enable movement of the steering cables or wires without leakage of fluid.

5. An endoscopic device connected to an insertion tube comprising an articulation section located at a distal end of the insertion tube, the device comprising:
    the handle of claim 1;
    a distal tip at the distal end of the insertion tube, and a plurality of tubes, wires, and cables passing through the interior of the insertion tube, and empty spaces between the plurality of tubes, wires, and cables, wherein the empty spaces are utilized as a channel which enables liquid or gas to flow from the handle to the distal tip.

6. The endoscopic device of claim 5, wherein the articulation section is located proximally to the distal tip of the insertion tube.

7. The endoscopic device of claim 5, wherein the articulation section is configured to be activated by cables or wires passing through tubes extending along the length of the interior of the insertion tube from the handle section to the articulation section.

8. The endoscopic device of claim 5, further comprising an imaging device located in the distal tip, the imaging device activated by power delivered to it and transmitting images gathered by it via one or more cables, wires, or optical fibers passing through one or more tubes extending the length of the interior of the insertion tube from the handle section to the distal tip.

9. The endoscopic device of claim 5, further comprising illumination devices located in the distal tip, the illumination devices activated by wires or optical fibers passing through one or more tubes extending the length of the interior of the insertion tube from the handle section to the distal tip.

10. The endoscopic device of claim 5, further comprising one or more working channels passing through the interior of the insertion tube from the handle section to the distal tip.

11. The endoscopic device of claim 5, further comprising one or more surgical tools each of which is located at a location on the insertion tube or on the distal tip and is associated with a tube, wires, or cable which passes through the interior of the insertion tube from the handle section to the location.

12. The handle of claim 1, wherein the one or more fluid sealed compartments are connected to a fluid inlet port for introducing fluid through the one or more fluid sealed compartments into the insertion tube.

13. The handle of claim 12, wherein said fluid is used for irrigation, insufflation, suction, cooling, heating, staining and/or therapy.

14. A method for reducing the diameter of an endoscopic device, the method comprising:
    providing an endoscope having a handle at its proximal end, the handle connected to an insertion tube having an articulation section at its distal end, wherein the articulation section is controlled through an articulation mechanism in the handle, the articulation mechanism including articulation wires or cables, wherein at least a portion of the articulation wires or cables are provided in one or more fluid sealed compartments in the handle, the one or more fluid sealed compartments being sealed relative to the handle to prevent leakage of liquid or gas from the one or more fluid sealed compartments into the handle while allowing the passage of liquid from the one or more fluid sealed compartments through the insertion tube;

connecting one or more of said one or more fluid sealed compartments in the handle to a fluid inlet port;

introducing fluid from the inlet port through the one or more fluid sealed compartments into empty spaces in the insertion tube without leakage of fluid out of the handle.

15. The method of claim 14, wherein the handle comprises of a base portion and a cover, the method further comprising pressing the cover against the base portion to form the one or more fluid sealed compartments in the handle.

16. The method of claim 14, wherein the one or more fluid sealed compartments are sealed by gaskets.

17. The method of claim 16, wherein the gaskets comprise at least one O-ring for sealing the one or more fluid sealed compartments and enabling movement of the steering cables or wires without leakage of fluid.

18. The method of claim 14, further comprising passing a plurality of tubes, wires, and cables through the interior of the insertion tube, and utilizing empty spaces between the plurality of tubes, wires, and cables as a channel which enables liquid or gas to flow from the handle to a distal tip located at the distal end of the insertion tube.

19. The method of claim 18, wherein utilizing the empty spaces as a channel comprises introducing liquid or gas through the handle to at least one nozzle at the distal tip of the insertion tube.

20. The method of claim 19, further comprising using the liquid or gas for one or more of: irrigation, insufflation, suction, cooling, heating, staining, and therapy.

* * * * *